(12) United States Patent
Haji et al.

(10) Patent No.: US 6,514,298 B2
(45) Date of Patent: Feb. 4, 2003

(54) FUEL ADDITIVE AND FUEL COMPOSITION

(75) Inventors: Katsuhiko Haji, Yokohama (JP); Masaki Nagao, Yokohama (JP); Tadahide Sone, Yokohama (JP)

(73) Assignee: Nippon Mitsubishi Oil Corporation, Tokyo (JP)

( * ) Notice: Subject to any disclaimer, the term of this patent is extended or adjusted under 35 U.S.C. 154(b) by 0 days.

(21) Appl. No.: 09/747,655

(22) Filed: Dec. 26, 2000

(65) Prior Publication Data

US 2001/0005957 A1 Jul. 5, 2001

(30) Foreign Application Priority Data

Dec. 27, 1999 (JP) ............................................ 11-371506

(51) Int. Cl.⁷ ................................ C10L 1/22; C10L 1/18
(52) U.S. Cl. ............................. 44/420; 564/248; 540/1; 540/450; 540/467; 540/470; 540/484; 540/544; 540/605; 544/1; 544/63; 544/106; 544/358; 546/1; 546/184
(58) Field of Search ........................... 44/420; 564/248; 544/1, 63, 106, 358; 546/1, 184; 540/1, 450, 467, 470, 484, 544, 605

(56) References Cited

U.S. PATENT DOCUMENTS

| | | | | | |
|---|---|---|---|---|---|
| 2,641,538 | A | * | 9/1953 | Thompson | 44/420 |
| 3,199,964 | A | * | 8/1965 | Arkell | 44/420 |
| 3,322,797 | A | * | 5/1967 | Holm | 554/105 |
| 4,003,719 | A | * | 1/1977 | McCoy | 44/420 |
| 4,160,648 | A | | 7/1979 | Lewis et al. | |
| 4,247,301 | A | | 1/1981 | Honnen | |
| 5,162,049 | A | * | 11/1992 | Bostick et al. | 44/335 |
| 5,312,849 | A | * | 5/1994 | Akita | 523/351 |
| 5,372,614 | A | * | 12/1994 | Kitahara | 44/371 |

\* cited by examiner

*Primary Examiner*—Cephia D. Toomer
(74) *Attorney, Agent, or Firm*—Akin, Gump, Strauss, Hauer & Feld, L.L.P.

(57) ABSTRACT

Fuel additives comprise a compound having a group represented by the formula

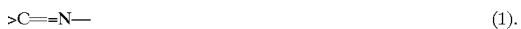

$$>C=N-\qquad(1).$$

Also disclosed are fuel compositions containing such additives. The additives have a superior detergent effect to conventional gasoline detergents and an excellent detergency of the injection nozzles of a diesel engine and is free from being sludge.

5 Claims, No Drawings

FUEL ADDITIVE AND FUEL COMPOSITION

BACKGROUND OF THE INVENTION

1. Field of the Invention

This invention relates to fuel additives and more particularly to fuel additives having excellent solubility in fuel and detergency in intake systems and combustion chambers of gasoline engines and in nozzles of diesel engines. This invention also relates to fuel compositions containing such additives.

2. Description of the Prior Art

Sludge or other objectionable deposits if formed in internal combustion engine fuel systems or combustion chambers of automobiles are responsible for engine trouble of abnormal rise in carbon monoxide and unburned hydrocarbon concentrations in the exhaust gases. It has thus far been proposed to use certain fuel additives, typically a gasoline detergent such as a polyetheramine-based or polyolefin-based detergent for removing or otherwise preventing deposits in the carburetors, electronic fuel injections, intake valves and other operative parts of automobiles.

Fuel additives to this end are disclosed in U.S. Pat. Nos. 4,247,301 and 4,160,648 wherein a polyether-based gasoline detergent is recited as being effective in removing or preventing deposits particularly on the fuel intake valves.

Intensive research efforts have been made in the automobile industry to eliminate or alleviate the adverse effect of exhaust gases upon human body and the environment together with the effort for fuel consumption reduction. However, since the conventional polyether amine-based or polyolefin-based gasoline detergents which can exhibit superior performances in removing or preventing deposits in intake valves but have tendency to increase deposits in combustion chambers, an overall improvement in exhaust gas has not been achieved yet. With this background in view, there has been a growing demand for more effective and advantageous fuel additives which are more excellent in detergency in the intake system and combustion chamber of a gasoline engine and which can exhibit a detergent capability even when the engine is under cold conditions.

It has also been pointed out that in a diesel engine deposits formed in the injection nozzles cause changes and delays in fuel flow rate, resulted in deteriorated running performance and exhaust gas. Therefore, there has also been demanded for fuel additives for diesel engines having superior detergent effects as well.

In view of the foregoing current situations, the present invention is intended to provide a novel fuel additive which exhibits superior performances over those of the conventional gasoline detergents and excels in detergency in the injection nozzles of a diesel engine as well as being itself free from becoming sludge.

BRIEF SUMMARY OF THE INVENTION

After intensive research and efforts made to develop a fuel additive having superior detergency in the intake system and combustion chamber of a gasoline engine as well as in the injection nozzles of a diesel engine, it was found that a compound having a group represented by formula (1) below exhibits superior performances to conventional gasoline detergents.

According to the present invention, there is provided a fuel additive which comprises a compound having a group represented by formula (1) below. According to another aspect of the present invention, there is provided a fuel composition which is obtained by adding a fuel additive comprising a compound having a group of formula (1) below to an internal combustion fuel

  (1)

DETAILED DESCRIPTION OF THE INVENTION

The present invention is described in more detail below.

The fuel additive of the present invention comprises a compound having a group represented by the formula

  (1)

A compound having a group of formula (1) is usually obtained by reacting a primary amine and a carbonyl compound.

The compound having a group of formula (1) is exemplified by ones represented by the formula (2)

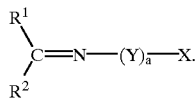

In formula (2), $R^1$ and $R^2$ are each independently either hydrogen or a hydrocarbon group having 1 to 30 carbon atoms. X is a group selected from groups of X1, X2, and X3. Y is a group selected from groups of Y1, Y2, Y3, and Y4. "a" is an integer of 0 or 1.

X1 is a group represented by the formula $$-(AO)_b-R^3 \quad (3)$$

wherein A is an alkylene group having 1 to 18 carbon atoms, b is an integer from 0 to 200, $R^3$ is either hydrogen or a hydrocarbon group having 1 to 300 carbon atoms.

X2 is a nitrogen-containing group represented by the formula (4)

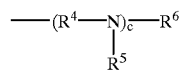

wherein $R^4$ is an alkylene group having 2 to 6 carbon atoms, $R^5$ is either hydrogen, an alkyl group having 1 to 4 carbon atoms, or a group of formula (3) provided that b is not 0, $R^6$ is either hydrogen, a hydrocarbon group having 1 to 300 carbon atoms, or a group of formula (3) wherein b is not 0, and c is an integer from 1 to 5.

X3 is a group having a nitrogen-containing cyclic compound residue represented by the formula (5)

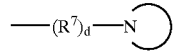

wherein $R^7$ is an alkylene group having 2 to 6 carbon atoms, the cyclic compound may have oxygen other than hydrogen, carbon, and nitrogen, and d is an integer of 0 or 1.

Y1 is a group represented by the formula

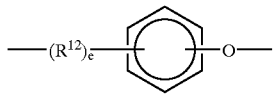
(6)

wherein $R^{12}$ is an alkylene group having 2 to 6 carbon atoms, and e is an integer of 0 or 1.

Y2 is a group represented by the formula

(7)

wherein $R^{13}$ is an alkylene group having 2 to 6 carbon atoms, and f is an integer of 0 or 1.

Y3 is a group represented by the formula

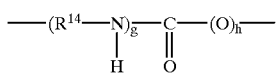
(8)

wherein $R^{14}$ is an alkylene group having 2 to 6 carbon atoms, g is an integer from 1 to 5, and h is an integer of 0 or 1.

Y4 is a group represented by the formula

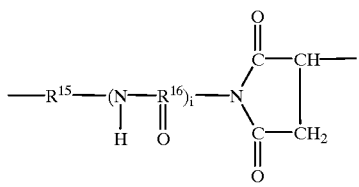
(9)

wherein $R^{15}$ and $R^{16}$ are each independently an alkylene group having 2 to 6 carbon atoms, and i is an integer from 0 to 5.

In formula (2), $R^1$ and $R^2$ are each independently hydrogen or a hydrocarbon group having 1 to 30 carbon atoms but is preferably a straight or branched alkyl group having 1 to 24 carbon atoms, a cycloalkyl or alkylcycloalkyl group, i.e., cycloalkyl substituted by alkyl, having 5 to 13 carbon atoms, a straight or branched alkenyl group having 2 to 24 carbon atoms, an aryl or alkylaryl group, i.e., aryl substituted by alkyl, having 6 to 18 carbon atoms, or an arylalkyl group, i.e., alkyl substituted by aryl, having 7 to 19 carbon atoms.

Preferred alkyl groups for $R^1$ and $R^2$ are methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl, straight or branched decyl, straight or branched undecyl, straight or branched dodecyl, straight or branched tridecyl, straight or branched tetradecyl, straight or branched pentadecil, straight or branched hexadecyl, straight or branched heptadecyl, straight or branched octadecyl, straight or branched nonadecyl, straight or branched eicosyl, straight or branched heneicosyl, straight or branched docosyl, straight or branched tricosyl, and straight or branched tetracosyl groups.

Preferred cycloalkyl groups for $R^1$ and $R^2$ are cyclopentyl, cyclohexyl, and cycloheptyl groups.

Preferred alkylcycloalkyl groups are metylcyclopentyl, dimethylcyclopentyl (including all positional isomers), ethylcyclopentyl (including all positional isomers), straight or branched propylcyclopentyl (including all positional isomers), ethylmethylcyclopentyl (including all positional isomers), trimethylcyclopentyl (including all positional isomers), diethylcyclopentyl (including all positional isomers), ethyldimethylcyclopentyl (including all positional isomers), straight or branched propylmethylcyclopentyl (including all positional isomers), straight or branched propylethylcyclopentyl (including all positional isomers), straight or branched dipropylcyclopentyl (including all positional isomers), straight or branched propylethylmethylcyclopentyl (including all positional isomers), methylcyclohexyl (including all positional isomers), dimethylcyclohexyl (including all positional isomers), ethylcyclohexyl (including all positional isomers), straight or branched propylcyclohexyl (including all positional isomers), ethylmethylcyclohexyl (including all positional isomers), trimethylcyclohexyl (including all positional isomers), diethylcyclohexyl (including all positional isomers), ethyldimethylcyclohexyl (including all positional isomers), straight or branched propylmethylcyclohexyl (including all positional isomers), straight or branched prorpylethylcyclohexyl (including all positional isomers), straight or branched dipropylcyclohexyl (including all positional isomers), straight or branched propylethylmethylcyclohexyl (including all positional isomers), methylcycloheptyl (including all positional isomers), dimethylcycloheptyl (including all positional isomers), ethylcycloheptyl (including all positional isomers), straight or branched propylcycloheptyl (including all positional isomers), ethylmethylcycloheptyl (including all positional isomers), trimethylcycloheptyl (including all positional isomers), diethylcycloheptyl (including all positional isomers), ethyldimethylcycloheptyl (including all positional isomers), straight or branched propylmethylcycloheptyl (including all positional isomers), straight or branched propylethylcycloheptyl (including all positional isomers), straight or branched dipropylcycloheptyl (including all positional isomers), and straight or branched propylethylmethylcycloheptyl (including all positional isomers) groups.

Preferred alkenyl groups for $R^1$ and $R^2$ are vinyl, propenyl, isopropenyl, straight or branched butenyl, butadienyl, straight or branched pentenyl, straight or branched hexenyl, straight or branched heptenyl, straight or branched octenyl, straight or branched nonenyl, straight or branched undecenyl, straight or branched decenyl, straight or branched dodecenyl, straight or branched tridecenyl, straight or branched tetradecenyl, straight or branched pentadecanyl, straight or branched hexadecenyl, straight or branched heptadecenyl, straight or branched octadecenyl such as oleyl, straight or branched nonedecenyl, straight or branched eicosenyl, straight or branched heneicosenyl, straight or branched docosenyl, straight or branched tricosenyl, and straight or branched tetracosenyl groups.

Preferred aryl groups for $R^1$ and $R^2$ are phenyl and naphthyl groups. Preferred alkylaryl groups are tolyl (including all positional isomers), xylyl (including all positional isomers), ethylphenyl (including all positional isomers), straight or branched propylphenyl (including all positional isomers), ethylmethylphenyl (including all positional isomers), trimethylphenyl (including all positional isomers), straight or branched butylphenyl (including all positional isomers), straight or branched propylmethylphenyl (including all positional isomers), diethylphenyl (including all positional isomers), ethyldimethylphenyl (including all positional isomers), tetramethylphenyl (including all positional isomers), straight or branched pentylphenyl (including all positional isomers), straight or branched hexylphenyl (including all positional isomers), straight or branched heptylphenyl (including all positional isomers), straight or branched octylphenyl (including all positional isomers), straight or branched nonylphenyl (including all positional isomers), straight or branched decylphenyl (including all positional isomers), straight or branched undecylphenyl (including all positional isomers), and straight or branched dodecylphenyl (including all positional isomers) groups. Preferred arylalkyl groups are benzyl, methylbenzyl (including all positional isomers), dimethylbenzyl (including all positional isomers), phenethyl, methylphenethyl (including all positional isomers), and dimethylphenethyl (including all positional isomers) groups.

Among these, more preferred for each $R^1$ and $R^2$ are hydrogen, a straight or branched alkyl group having 1 to 12 carbon atoms, and an aryl or alkylaryl group having 6 to 18 carbon atoms. Most preferred are a straight or branched alkyl group having 1 to 6 carbon atoms, a phenyl group, and a straight or branched alkylaryl group having 7 to 15 carbon atoms.

A carbonyl compound used to obtain a compound of formula (2) is an aldehyde compound in the case where at least one of $R^1$ and $R^2$ is hydrogen, and a ketone compound in the case where both of $R^1$ and $R^2$ are hydrocarbon groups.

Specific examples of such an aldehyde compound are formaldehyde, acetaldehyde, butylaldehyde, and benzaldehyde. Specific examples of such a ketone compound are acetone, methyl ethyl ketone, methyl-n-propyl ketone, methyl isopropyl ketone, methyl butyl ketone (including all isomers), methyl pentyl ketone (including all isomers), methyl hexyl ketone (including all isomers), methyl heptyl ketone (including all isomers), methyl octyl ketone (including all isomers), diethyl ketone, ethyl-n-propyl ketone, ethyl isopropyl ketone, ethyl butyl ketone (including all isomers), ethyl pentyl ketone (including all isomers), ethyl hexyl ketone (including all isomers), ethyl heptyl ketone (including all isomers), ethyl octyl ketone (including all isomers), dipropyl ketone (including all isomers), propyl butyl ketone (including all isomers), propyl pentyl ketone (including all isomers), propyl hexyl ketone (including all isomers), propyl heptyl ketone (including all isomers), propyloctyl ketone (including all isomers), dibutyl ketone (including all isomers), butyl pentyl ketone (including all isomers), butyl hexyl ketone (including all isomers), butyl heptyl ketone (including all isomers), butyl octyl ketone (including all isomers), acetophenone, propiophenone, benzophenone, 2-methyl naphthone, 2-ethyl naphthone, 2-benzonaphtone, methyl benzyl ketone, ethyl benzyl ketone, propyl benzyl ketone (including all isomers), butyl benzyl ketone (including all isomers), cyclopentanone, cyclohexanone, cycloheptanone, and cyclooctanone.

Next, groups of X1 through X3 represented by X in formula (2) are described in this order.

X1 is a group represented by the formula

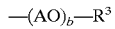 (3)

wherein A is an alkylene group having 1 to 18 carbon atoms, b is an integer from 0 to 200, $R^3$ is either hydrogen or a hydrocarbon group having 1 to 300 carbon atoms.

Examples of a hydrocarbon group having 1 to 300 carbon atoms represented by $R^3$ are those already exemplified with respect to $R^1$ and $R^2$, such as straight or branched alkyl groups having 1 to 24 carbon atoms, cycloalkyl or alkylcycloalkyl groups having 5 to 13 carbon atoms, straight or branched alkenyl groups having 2 to 24 carbon atoms, aryl or alkylaryl groups having 6 to 18 carbon atoms, and arylalkyl groups having 7 to 19 carbon atoms. $R^3$ may be a residue derived from an olefin polymer having a weight-average molecular weight of 300 to 4,200, preferably 500 to 3,000, such as ethylene, propylene, 1-butylene, 2-butylene and isobutylene.

$R^3$ is preferably hydrogen, a straight or branched alkyl group having 1 to 12 carbon atoms, a cycloalkyl group, an aryl or alkylaryl group having 6 to 18 carbon atoms, or a residue derived from polypropylene having a weight-average molecular weight of 500 to 3,000 or from polyisobutylene having a weight-average molecular weight of 500 to 3,000. $R^3$ is more preferably hydrogen, a straight or branched alkyl group having 1 to 6 carbon atoms, a cyclohexyl group, a phenyl group, an alkylaryl group having 7 to 15 carbon atoms, or a residue derived from polyisobutylene having a weight-average molecular weight of 700 to 2,000. $R^3$ is most preferably hydrogen or a residue derived from polyisobutylene having a weight-average molecular weight of 700 to 1,500.

"A" in formula (3) is an alkylene group having 2 to 18 carbon atoms, preferably having 2 to 6 carbon atoms, and more preferably having 2 to 4 carbon atoms. Specific examples of the alkylene group having 2 to 4 carbon atoms are ethylene, propylene (1-methylethylene, 2-methylethylene), butylene (1-ethylethylene, 2-ethylethylene), 1,2-dimethylethylene, 1,1-dimethylethylene, and 2,2-dimethylethylene groups.

In the case where b is 2 or greater, a plurality of "A" groups may be the same or different in the same molecule.

(AO) in formula (3) indicates the main chain derived from an alkyleneoxide. Specific examples of the alkyleneoxides are ethyleneoxide, propyleneoxide, 1,2-butyleneoxide, 2,3-butyleneoxide and isobutyleneoxide. These alkyleneoxides may be homopolymers, or random- or block-copolymers thereof.

"b" in formula (3) is an integer from 0 to 200, preferably 0 to 100.

In the case where b is not 0, $R^3$ is preferably hydrogen, a straight or branched alkyl group having 1 to 24 carbon atoms, a cycloalkyl or alkylcycloalkyl group having 5 to 13 carbon atoms, a straight or branched alkenyl group having 2 to 24 carbon atoms, an aryl or alkylaryl group having 6 to 18 carbon atoms, or an arylalkyl group having 7 to 19 carbon atoms; more preferably hydrogen, a straight or branched alkyl group having 1 to 12 carbon atoms, a cycloalkyl group having 5 to 7 carbon atoms, or an aryl or alkylaryl group having 6 to 18 carbon atoms; still more preferably hydrogen, a straight or branched alkyl group having 1 to 6 carbon atoms, cyclohexyl, phenyl, or an alkylaryl group having 7 to 15 carbon atoms; and most preferably hydrogen.

X2 is a nitrogen-containing group represented by the formula

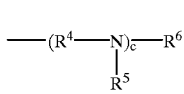 (4)

wherein $R^4$ is an alkylene group having 2 to 6 carbon atoms, $R^5$ is either hydrogen, an alkyl group having 1 to 4 carbon atoms, or a group of formula (3) wherein b is not 0, $R^6$ is either hydrogen, a hydrocarbon group having 1 to 300 carbon atoms, or a group of formula (3) provided that b is not 0, and c is an integer from 1 to 5.

$R^4$ in formula (4) is an alkylene group having 2 to 6 carbon atoms. Specific examples of such an alkylene group are ethylene, propylene (1-methylethlene, 2-methylethlene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene, tetramethylene, pentylene (1-butylethylene, 2-butylethylene), 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, hexylenen (1-butylethylene, 2-butylethylene), 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 1-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimetyltrimethylene, 1,1,3-trimetyltrimethylene, 1,2,2-trimetyltrimethylene, 1,2,3-trimetyltrimethylene, 1,3,3-trimetyltrimethylene, 2,2,3-trimetyltrimethylene, 2,3,3-trimetyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene, and hexamethylene groups.

Among these, $R^4$ is preferably an alkylene group having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferably an alkylene group having 2 or 3 carbon atoms, such as ethylene, propylene (1-methylethylene, 2-methylethylene) and trimethylene groups.

$R^5$ in formula (4) is either hydrogen, an alkyl group having 1 to 4 carbon atoms, or a group of formula (3) provided that b is not 0. Specific examples of such an alkyl group are methyl, ethyl, n-propyl, isopropyl, n-butyl, isobutyl, sec-butyl, and tert-butyl groups. Among these, $R^5$ is preferably hydrogen, an alkyl group having 1 to 3 carbon atoms, or a group of formula (3) provided that b is not 0, and more preferably hydrogen, methyl or ethyl group.

$R^6$ in formula (4) is either hydrogen, a hydrocarbon group having 1 to 300 carbon atoms, or a group of formula (3) provided that b is not 0. Specific examples of such a hydrocarbon group are those already exemplified with respect to $R^1$ and $R^2$, such as straight or branched alkyl groups having 1 to 24 carbon atoms, cycloalkyl or alkylcycloalkyl groups having 5 to 13 carbon atoms, straight or branched alkenyl groups having 2 to 24 carbon atoms, aryl or alkylaryl groups having 6 to 18 carbon atoms, and arylalkyl groups having 7 to 19 carbon atoms. $R^6$ may be a residue derived from an olefin polymer having a weight-average molecular weight of 300 to 4,200, preferably 500 to 3,000, such as ethylene, propylene, 1-butylene, 2-butylene and isobutylene.

$R^6$ is preferably hydrogen, a straight or branched alkyl group having 1 to 12 carbon atoms, an aryl or alkylaryl group having 6 to 18 carbon atoms, a residue derived from polypropylene having a weight-average molecular weight of 500 to 3,000 or from polyisobutylene having a weight-average molecular weight of 500 to 3,000, or a group of formula (3) provided that b is not 0. $R^6$ is more preferably hydrogen, a straight or branched alkyl group having 1 to 6 carbon atoms, a phenyl group, an alkylaryl group having 7 to 15 carbon atoms, a residue derived from polyisobutylene having a weight-average molecular weight of 700 to 2,000, or a group of formula (3) provided that b is not 0.

"c" in formula (4) is an integer from 1 to 5, preferably from 1 to 4, and more preferably from 1 to 3.

A group represented by formula (10) contained in a group of formula (4) has 1 to 5, preferably 1 to 4, and more preferably 1 to 3 constituting units represented by formula (11):

wherein $R^4$, $R^5$ and c are as defined in formula (4).

Therefore, the group of formula (10) is a group which may be comprised of constituting units of formula (11) in the following manner:

(1) homopolymer of one kind of the constituting unit of formula (11), and
(2) random-, alternating- or block bonded polymer of more than one kind of constituting units of formula (11).

Preferred nitrogen-containing groups of formula (4) are those of formula (4) wherein $R^4$ is an alkylene group having 2 to 4 carbon atoms, $R^5$ is either hydrogen, an alkyl group having 1 to 3 carbon atoms, or a group of formula (3) provided that b is not 0, $R^6$ is either hydrogen, a straight or branched alkyl group having 1 to 12 carbon atoms, an aryl or alkylaryl group having 6 to 18 carbon atoms, a residue derived from polypropylene having a weight-average molecular weight of 500 to 3,000 or from polyisobutylene having a weight-average molecular weight of 500 to 3,000, or a group of formula (3) provided that b is not 0, and c is an integer from 1 to 4. The most preferred are those of formula (4) wherein $R^4$ is either ethylene, propylene (1-methylethylene, 2-methylethylene), or trimethylene group, $R^5$ is either hydrogen, methyl or ethyl group, or a group of formula (3) provided that b is not 0, $R^6$ is either hydrogen, an alkyl group having 1 to 6 carbon atoms, phenyl group, a straight or branched alkylaryl group having 7 to 15 carbon atoms, a residue derived from polyisobutylene having a weight-average molecular weight of 700 to 2,000, or a group of formula (3) provided that b is not 0, and c is an integer from 1 to 3.

In the case where both $R^5$ and $R^6$ are hydrogen, amino groups are present at the terminal ends. These amino groups are reacted with carbonyl groups, and the resulting compound has two group of formula (1) in one molecule as represented by the formula

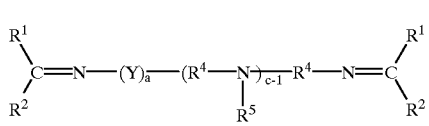

(12)

wherein $R^1$, $R^2$, Y, and a are as defined in formula (2), and $R^4$, $R^5$, and c are as defined in formula (4).

Such a compound is also within the scope of the present invention.

X3 is a group having a nitrogen-containing cyclic compound residue, represented by the formula

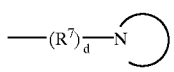

(5)

wherein $R^7$ is an alkylene group having 2 to 6 carbon atoms, the cyclic compound may have oxygen other than hydrogen, carbon, and nitrogen, and d is an integer of 0 or 1.

$R^7$ in formula (5) is an alkylene group having 2 to 6 carbon atoms. Specific examples of such an alkylene group are those exemplified with respect to $R^4$. Among these, $R^4$ is preferably an alkylene group having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferably an alkylene group having 2 or 3 carbon atoms, such as ethylene, propylene (1-methylethylene, 2-methylethylene) and trimethylene groups.

A group of formula (5) has a residue of a nitrogen-containing cyclic compound represented by the formula

(13)

The nitrogen-containing cyclic compound may have oxygen other than carbon and nitrogen as the ring-constituting atom. The cyclic compound may be a 5-, 6- or 7-membered ring but is preferably a 5- or 6-membered ring. The cyclic compound may have a double bond in a ring.

Specific examples of the cyclic compound are pyrrole, piperidine, piperazine, and morpholine. Among these, preferred are piperidine, piperazine, and morpholine.

Other than these compounds, a compound of formula (13) may be the above-mentioned cyclic compounds bonding to a hydrocarbon group having 1 to 10 carbon atoms.

The hydrocarbon group having 1 to 10 carbon atoms may be a straight or branched alkyl group having 1 to 10 carbon atoms, a cycloalkyl or alkylcycloalkyl group having 5 to 10 carbon atoms, a straight or branched alkenyl group having 2 to 10 carbon atoms, and an aryl or alkylaryl group having 6 to 10 carbon atoms, and an arylalkyl group having 7 to 10 carbon atoms.

Specific examples of the alkyl group are methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl, and straight or branched decyl groups.

Specific examples of the cycloalkyl group are cyclopentyl, cyclohexyl, and cycloheptyl groups. Preferred alkylcycloalkyl groups are metylcyclopentyl, dimethylcyclopentyl (including all positional isomers), ethylcyclopentyl (including all positional isomers), straight or branched propylcyclopentyl (including all positional isomers), ethylmethylcyclopentyl (including all positional isomers), trimethylcyclopentyl (including all positional isomers), diethylcyclopentyl (including all positional isomers), ethyldimethylcyclopentyl (including all positional isomers), straight or branched propylmethylcyclopentyl (including all positional isomers), straight or branched propylethylcyclopentyl (including all positional isomers), methylcyclohexyl (including all positional isomers), dimethylcyclohexyl (including all positional isomers), ethylcyclohexyl (including all positional isomers), straight or branched propylcyclohexyl (including all positional isomers), ethylmethylcyclohexyl (including all positional isomers), trimethylcyclohexyl (including all positional isomers), diethylcyclohexyl (including all positional isomers), ethyldimethylcyclohexyl (including all positional isomers), straight or branched propylmethylcyclohexyl (including all positional isomers), methylcycloheptyl (including all positional isomers), dimethylcycloheptyl (including all positional isomers), ethylcycloheptyl (including all positional isomers), straight or branched propylcycloheptyl (including all positional isomers), ethylmethylcycloheptyl (including all positional isomers), trimethylcycloheptyl (including all positional isomers).

Specific examples of the alkenyl groups are vinyl, propenyl, isopropenyl, straight or branched butenyl, butadienyl, straight or branched pentenyl, straight or branched hexenyl, straight or branched heptenyl, straight or branched octenyl, straight or branched nonenyl, and straight or branched decenyl.

Specific examples of the aryl group are phenyl and naphthyl groups. Specific examples of the alkylaryl group are tolyl (including all positional isomers), xylyl (including all positional isomers), ethylphenyl (including all positional isomers), straight or branched propylphenyl (including all positional isomers), ethylmethylphenyl (including all positional isomers), trimethylphenyl (including all positional isomers), straight or branched butylphenyl (including all positional isomers), straight or branched propylmethylphenyl (including all positional isomers), diethylphenyl (including all positional isomers), ethyldimethylphenyl (including all positional isomers), and tetramethylphenyl (including all positional isomers). Preferred arylalkyl groups are benzyl, methylbenzyl (including all positional isomers), dimethylbenzyl (including all positional isomers), phenethyl, methylphenethyl (including all positional isomers), and dimethylphenethyl (including all positional isomers) groups.

The hydrocarbon group having 1 to 10 carbon atoms is preferably an alkyl group having 1 to 6 carbon atoms, and more preferably an alkyl group having 1 to 3 carbon atoms.

A group of formula (5) is preferably a group, wherein $R^7$ is an alkylene group having 2 to 4 carbon atoms and d is an integer of 0 or 1, having a residue of piperidine, piperazine, morpholine, or any of these compounds to which an alkyl group having 1 to 6 carbon atoms bonds. A group of formula (5) is most preferably a group wherein $R^7$ is ethylene or propylene (1-methylethylene, 2-methylethylene) group, and d is an integer of 0 or 1, having a residue of piperazine, morpholine, or any of these compounds to which an alkyl group having 1 to 3 carbon atoms bonds.

X in formula (2) is preferably a group of X1 or X2.

Next, Y1 through Y4 from which Y in formula (2) is selected are described below.

Y1 is a group represented by the formula

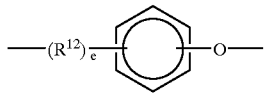

(6)

wherein $R^{12}$ is an alkylene group having 2 to 6 carbon atoms, and e is an integer of 0 or 1.

Specific examples of preferred alkylene groups for $R^{12}$ are those as already exemplified with respect to $R^4$. More specifically, preferred are alkylene groups having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferred are alkylene groups having 2 or 3 carbon atoms, such as ethylene, propylene (1-methylethylene, 2-methylethylene) and trimethylene groups.

"e" in formula (6) is an integer of 0 or 1.

Y2 is a group represented by the formula

(7)

wherein $R^{13}$ is an alkylene group having 2 to 6 carbon atoms, and f is an integer of 0 or 1.

Specific examples of preferred alkylene groups for $R^{13}$ are those as already exemplified with respect to $R^4$. More specifically, preferred are alkylene groups having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferred are alkylene groups having 2 or 3 carbon atoms such as, ethylene, propylene (1-methylethylene, 2-methylethylene) and trimethylene groups.

"f" in formula (7) is an integer of 0 or 1.

Y3 is a group represented by the formula

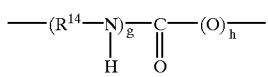

(8)

wherein $R^{14}$ is an alkylene group having 2 to 6 carbon atoms, g is an integer from 1 to 5, and h is an integer of 0 or 1.

Specific examples of preferred alkylene groups for $R^{14}$ are those as already exemplified with respect to $R^4$. More specifically, preferred are alkylene groups having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferred are alkylene groups having 2 or 3 carbon atoms, such as ethylene, propylene (1-methylethylene, 2-methylethylene) and trimethylene groups.

"g" in formula (8) is an integer from 1 to 5, preferably 1 to 4, more preferably 1 to 3. "h" in formula (8) is an integer of 0 or 1.

Y4 is a group represented by the formula

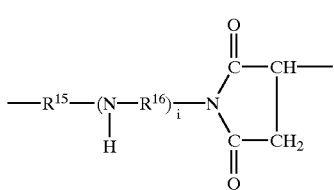

(9)

wherein $R^{15}$ and $R^{16}$ are each independently an alkylene group having 2 to 6 carbon atoms, and i is an integer from 0 to 5.

Specific examples of preferred alkylene groups for $R^{15}$ and $R^{16}$ are those as already exemplified with respect to $R^4$. More specifically, preferred are alkylene groups having 2 to 4 carbon atoms, such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene groups, and more preferred are alkylene groups having 2 or 3 carbon atoms, such as ethylene, propylene (1-methylethylene, 2-methylethylene), and trimethylene groups.

"i" in formula (9) is an integer from 0 to 5, preferably 0 to 4, and more preferably 0 to 3.

Preferred compounds having a group of formula (1) are those represented by formula (2) wherein $R^1$ and $R^2$ are each independently hydrogen, a straight or branched alkyl group having 1 to 12 carbon atoms, or an aryl or alkylaryl having 6 to 18 carbon atoms, X is a group selected from groups of X1 through X3, Y is a group selected from groups of Y1 through Y4, and a is an integer of 0 or 1;

X1 being a group of formula (3) wherein $R^3$ is either hydrogen, a straight or branched alkyl group having 1 to 12 carbon atoms, a cycloalkyl group, an aryl or alkylaryl group having 6 to 18 carbon atoms, or a residue derived from polypropylene having a weight-average molecular weight of 500 to 3,000 or from polyisobutylene having a weight-average molecular weight of 500 to 3,000, A is an alkylene group having 2 to 6 carbon atoms, and b is an integer from 0 to 200, X2 being a group of formula (4) wherein $R^4$ an alkylene group having 2 to 4 carbon atoms, $R^5$ is either hydrogen, an alkyl group having 1 to 3 carbon atoms, or a group of formula (3) provided that b is not 0, $R^6$ is either hydrogen, a straight or branched alkyl group having 1 to 12 carbon atoms, an aryl or alkylaryl group having 6 to 18 carbon atoms, a residue derived from polypropylene having a weight-average molecular weight of 500 to 3,000 or from polyisobutylene having a weight-average molecular weight of 500 to 3,000, or a group of formula (3) provided that b is not 0, and c is an integer from 1 to 4, X3 being a group of formula (5) wherein $R^7$ is an alkylene group having 2 to 4 carbon atoms, the nitrogen-containing cyclic compound residue is a residue of either piperidine, piperadine, morpholine, or any one of these compounds to which an alkyl group having 1 to 6 carbon atoms bonds, and d is an integer of 0 or 1; and Y1 being a group of formula (6) wherein $R^{12}$ is an alkylene group having 2 to 4 carbon atoms, and e is an integer of 0 or 1, Y2 being a group of formula (7) wherein $R^{13}$ is an alkylene group having 2 to 4 carbon atoms, and f is an integer of 0 or 1, Y3 being a group of formula (8) wherein $R^{14}$ is an alkylene group having 2 to 4 carbon atoms, g is an integer from 1 to 4, and h is an integer of 0 or 1, and Y4 being a group of formula (9) wherein $R^{15}$ and $R^{16}$ are each independently an alkylene group having 2 to 4 carbon atoms, and i is an integer from 0 to 4.

More preferred compounds having a group of formula (1) are those represented by formula (2) wherein $R^1$ and $R^2$ are each independently a straight or branched alkyl group having 1 to 6 carbon atoms, a phenyl group, a straight or branched alkylaryl group having 7 to 15 carbon atoms, X is a group of either X1 or X2, Y is a group selected from Y1 through Y4 groups, and a is an integer of 0 or 1;

X1 being a group of formula (3) wherein $R^3$ is either hydrogen, a straight or branched alkyl group having 1 to 6 carbon atoms, a cycloalkyl group, a phenyl group, an alkylaryl group having 7 to 15 carbon atoms, or a residue derived from polyisobutylene having a weight-average molecular weight of 700 to 2,000, A is an alkylene group having 2 to 4 carbon atoms, and b is an integer from 0 to 100, and X2 being a group of formula (4) wherein $R^4$ is either ethylene, propylene (1-methylethylene, 2-methylethylene) or trimethylene group, $R^5$ is either hydrogen, methyl, ethyl group, or a group of formula (3) provided that b is not 0, $R^6$ is either hydrogen, a straight or branched alkyl group having 1 to 6 carbon atoms, a phenyl group, an alkylaryl group having 7 to 15 carbon atoms, a residue derived from polyisobutylene having a weight-average molecular weight of 700 to 2,000, or a group of formula (3) provided that b is not 0, and c is an integer from 1 to 3; and Y1 being a group of formula (6) wherein e is 0, Y2 being a group of formula (7) wherein f is 0, Y3 being a group of formula (8) wherein $R^{14}$ is either ethylene, propylene (1-methylehtylene, 2-methylethylene), or trimethylene group, g is an integer from 1 to 3, and h is 1, and Y4 being a group of formula (9) wherein $R^{15}$ and $R^{16}$ are each independently either ethylene, propylene (1-methylehtylene, 2-methylethylene), or trimethylene group, and i is an integer from 0 to 3.

The most preferred compounds having a group of formula (1) are those represented by formula (2) wherein $R^1$ and $R^2$ are each independently a straight or branched alkyl group having 1 to 4 carbon atoms, a phenyl group, a straight or branched alkylaryl group having 7 to 15 carbon atoms, X is a X1 group, Y is a group of either Y1 or Y3, and a is an integer of 0 or 1;

X1 being a group of formula (3) wherein $R^3$ is either hydrogen, a straight or branched alkyl group having 1 to 6 carbon atoms, a cyclohexyl group, a phenyl group, an alkylaryl group having 7 to 15 carbon atoms, or a residue derived from polyisobutylene having a weight-average molecular weight of 700 to 1,500, A is an alkylene group having 2 to 4 carbon atoms, and b is an integer from 0 to 100; and Y1 being a group of formula (6) wherein e is 0, and Y3 being a group of formula (8) wherein $R^{14}$ is either ethylene or propylene (1-methylethylene, 2-methylethylne) group, g is an integer of 1 or 2, and h is 1.

A compound having a group of formula (1) according to the present invention may be produced by any suitable method. For instance, the compound of the present invention may be produced by heating and dehydrating a compound of formula (14) below having a primary amino group in the molecule and a compound of formula (15) below having a carbonyl group in the molecule:

wherein X, Y and a are as defined in formula (2), and $R^1$ and R are as defined in formula (2).

The reaction is carried out using equimolecular amounts of a compound of formula (14) and a compound of formula (15). However, in order to accelerate the reaction, the reaction is preferably carried out by adding 1.0 to 10.0 mole times of excess compound having a carbonyl group which can easily remove the unreacted products after the reaction. The reaction temperature is not restricted but is usually within the range from 40 to 180° C., preferably 80 to 150° C.

The additive comprised of a compound having a group of formula (1) of the present invention is used as a fuel additive. The additive of the present invention is significantly useful as a gasoline- and gas oil- additive and is added to a base gasoline or to a gasoline composition obtained by mixing a base gasoline with other gasoline additive, or if necessary to a gas oil composition obtained by mixing a base gas oil with other gas oil additives.

The additive of the present invention is also significantly useful as a gasoline additive for direct injection gasoline engines as well as direct injection diesel engines. Furthermore, the additive of the present invention may be blended in a gasoline composition for direct injection gasoline engine or in a gas oil composition for direct injection diesel engines.

Although not restricted, a gasoline- or gas oil composition contains the additive comprised of a compound having a group of formula (1) of the present invention in an amount of 0.001 to 10 mass percent, based on the total mass of the composition.

In order to enhance detergency in the intake system or the combustion chamber of a gasoline engine, in the nozzles of a diesel engine, and in the combustion chamber of a direct injection gasoline engine, particularly the cavity formed on the upper surface of the pistons, the lower limit of the content of the additive of the present invention is 0.001 mass percent, preferably 0.003 mass percent, more preferably 0.005 mass percent, even more preferably 0.01 mass percent, and most preferably 0.015 mass percent.

Because no further enhancement effect can be expected at higher concentrations of the additive, the upper limit of the additive content in a gasoline- or gas oil-composition is 10 mass percent, preferably 5 mass percent, more preferably 4 mass percent, and most preferably 3 mass percent.

The above-mentioned base gasoline may be prepared with various gasoline components using conventional known methods. Such components may be light naphtha derived from atmospheric distillation of crude oil, cracked gasoline derived from catalytic cracking or hydrocracking, reformed gasoline obtainable by catalytic reforming, polymerized gasoline by olefin-polymerization, alkylates derived from addition reaction or alkylation of a hydrocarbon such as isobutane with a lower olefin, isomerized gasoline derived from conversion of light naphtha into isoparaffin using an isomerization device, de-n-paraffinized oil, butane, aromatic hydrocarbons and paraffinic fractions derivable from hydrocracking dimerized propylene.

Shown below is a typical blend formulation of an unleaded gasoline.

(1) reformed gasoline: 0–70 vol. %
(2) light fractions of reformed gasoline (boiling at 25–120° C.): 0–35 vol. %
(3) heavy fractions of reformed gasoline (boiling at 110–200° C.): 0–45 vol. %
(4) cracked gasoline: 0–50 vol. %
(5) light fractions of cracked gasoline (boiling at 25–90° C.): 0–45 vol. %
(6) heavy fractions of cracked gasoline (boiling at 90–200° C.): 0–40 vol. %
(7) alkylate: 0–40 vol. %
(8) paraffin fraction derived from dimerization and subsequent hydrogenation of propylene: 0–30 vol. %
(9) isomerized gasoline: 0–30 vol. %
(10) MTBE: 0–15 vol. %
(11) light naphtha: 0–20 vol. %
(12) butane: 0–10 vol. %

If the benzene content of a base gasoline needs to be reduced, the reformed gasoline may be added in smaller amount because it contains more benzene than the other gasoline components. Alternatively, the content of benzene may be reduced by using a reformed gasoline which is reduced in the benzene content by any suitable methods given below:

(1) removing benzene fraction by distilling a reformed gasoline
(2) extracting benzene in a reformed gasoline with a solvent such as sulfolane
(3) converting benzene into another compound by the following methods (A), (B) or (C),
   (A) converting benzene by hydrogenating into cyclohexane, methylcyclohexane or the like,
   (B) converting benzene by reacting it with $C_9$ or greater aromatic hydrocarbon into toluene, xylene, ethylbenzene or the like
   (C) alkylating benzene with lower olefins such as ethylene and propylene or with lower alcohols such as methanol and ethanol,
(4) using a reformer feed of desulfurization heavy naphtha derived from removal of $C_6$ hydrocarbon by distillation, and
(5) controlling the operation conditions of a catalyst reforming apparatus.

A gasoline composition containing the additive of the present invention may contain other gasoline additives.

Specific examples of such gasoline additives which can be used in combination with the additive according to the present invention are detergent dispersants other than the above-described polyetheramines and polyethers, such as succinimide and polyalkylamine; phenol- or amine-based oxidation inhibitors; metal deactivators such as Schiff-type compounds and thioamide-type compounds; surface ignition preventers such as organophosphorus-derived compounds; antiicing agents such as polyalcohols and ethers thereof; combustion improvers such as alkali metal or alkaline earth metal salts of organic acids and sulfuric esters of higher alcohols; anistatic additives such as anionic surfactants, cationic surfactants and amphoteric surfactants; dyes such as azo dyes; corrosion inhibitors such as alkenyl succinate; identifying agents such as quinizarine and coumarin, and malodorants such as natural essential-based aromatics. One or more of these additives may be blended in a gasoline composition in an amount which is preferably 0.1 mass percent or less, based on the total mass of the gasoline composition.

No particular limitation is imposed on the properties and components of a gasoline composition containing a base gasoline, the additive of the present invention, and other additives blended as required. The gasoline composition will preferably exhibit the following distillation properties measured in accordance with JIS K 2254 "Petroleum products-Determination of distillation characteristics".

| | |
|---|---|
| Initial distillation boiling point (IBP 0) | 20–45° C. |
| Running point at 10 vol. % ($T_{10}$) | 35–55° C. |
| Running point at 30 vol. % ($T_{30}$) | 55–75° C. |
| Running point at 50 vol. % ($T_{50}$) | 75–100° C. |
| Running point at 70 vol. % ($T_{70}$) | 100–130° C. |
| Running point at 90 vol. % ($T_{90}$) | 110–160° C. |
| End point | 130–210° C. |

The lower limit of the initial point is preferably 20° C., and more preferably 25° C. An initial point of lower than 20° C. would lead to poor startability of an engine at higher temperatures. The upper limit of the initial point is preferably 45° C., more preferably 40° C., and further more preferably 35° C. An initial point which is higher than 45° C. would lead to poor startability of an engine at lower temperatures.

The lower limit of ($T_{10}$) is preferably 35° C., and more preferably 40° C. A ($T_{10}$) of lower than 35° C. would lead to poor startability of an engine at higher temperatures. The upper limit of ($T_{10}$) is preferably 55° C., more preferably 50° C., and further more preferably 48° C. A ($T_{10}$) of higher than 55° C. would lead to poor low-temperature drivability.

The lower limit of ($T_{30}$) is 55° C., and preferably 60° C. A ($T_{30}$) of lower than 55° C. would invite objectionable high temperature drivability and cause gasoline coking in engine injectors. The upper limit of ($T_{30}$) is 75° C., preferably 70° C. and more preferably 68° C. A ($T_{30}$) which is higher than 75° C. would lead to aggravated low-temperature drivability.

The lower limit of ($T_{50}$) is 75° C., and preferably 80° C. A ($T_{50}$) of lower than 75° C. would adversely affect high-temperature drivability. The upper limit of ($T_{50}$) is 100° C., preferably 95° C., and more preferably 93° C. A ($T_{50}$) which is higher than 100° C. would adversely affect low- and normal-temperature drivability.

The lower limit of ($T_{70}$) is 100° C., while the upper limit of ($T_{70}$) is 130° C., preferably 125° C., more preferably 123° C., and most preferably 120° C. A ($T_{70}$) which is higher than 130° C. would adversely affect low- and normal- temperature drivability.

The lower limit of ($T_{90}$) is 110° C., and preferably 120° C. A ($T_{90}$) of lower than 110° C. would cause reduced fuel consumption efficiency. The upper limit of ($T_{90}$) is 160° C., preferably 150° C., and more preferably 140° C. A ($T_{90}$)

which is higher than 160° C. would affect low- and normal-temperature drivability and cause the increase of exhaust gas emission, the deterioration of engine oil and the formation of sludge.

The lower limit of the end point is preferably 130° C., while the upper limit thereof is 210° C., preferably 200° C., more preferably 195° C., and most preferably 190° C. An end point which is higher than 210° C. would lead to poor drivability at normal temperatures.

The gasoline composition has a vapor pressure which is 70 kPa or less, preferably 65 kPa or less, more preferably 60 kPa or less, and most preferably 55 kPa or less in order to avoid the occurrence of coking in engine injectors and suppress the amount of evaporation emission. The term "vapor pressure" used herein denotes Reid vapor pressure (RVP) measured in accordance with JIS K 2258 "Testing Method for Crude Oil and Vapor Pressure of Petroleum Products (Reid Method)".

Although not restricted, the density at 15° C. of the gasoline composition is within the range of 0.73 to 0.77 g/cm$^3$. The lower limit of density is 0.73 g/cm$^3$, and preferably 0.735 g/cm$^3$, as density less than 0.73 g/cm$^3$ would decrease fuel consumption efficiency. The upper limit of density is 0.77 g/cm$^3$, and preferably 0.76 g/cm$^3$. Density in excess of 0.77 g/cm$^3$ would lead to insufficient acceleration and spark plug smoldering. The density used herein denotes a density determined by JIS K 2249 "Crude petroleum and petroleum products-Determination of density and petroleum measurement tables based on a reference temperature (15° C.)".

The gasoline composition is substantially free of alkyl lead compounds such as tetraethyl lead. Even though the gasoline composition contains very small amount of such lead compounds, the amount thereof is preferably held below the lower threshold specified by JIS K 2255 "Petroleum products-Gasoline-Determination of Lead Content".

The gasoline composition has a research octane number (RON) which is 89 or greater, preferably 90 or greater, more preferably 90.5 or greater, and most preferably 91 or greater. In order to enhance anti-knocking performance during high-speed driving, the gasoline composition should have a motor octane number (MON) which is 80 or greater, preferably 80.5 or greater, and most preferably 81 or greater. Both RON and MON denote the values measured in accordance with JIS K 2280 "Petroleum products-Fuels-Determination of octane number, cetane number and calculation of cetane index".

The contents of paraffins, olefins and aromatics in the gasoline composition according to the present invention are preferably as follows:

| | |
|---|---|
| Paraffins (V(P)) | 50–100 vol. % |
| Olefins (V(O)) | 0–15 vol. % |
| Aromatics (V(Ar)) | 0–35 vol. % |

(V(P)) of the gasoline composition is in the range of 50 to 100 percent by volume, preferably 60 to 100 percent by volume, more preferably 70 to 100 percent by volume with the objectives of precluding gasoline coking in the injectors of an engine, and reducing spark plug smoldering and the ozone-generation ability of exhaust gas as well as the concentration of benzene contained therein, and avoiding the generation of soot.

(V(O)) of the gasoline composition is in the range of 0 to 15 percent by volume, preferably 0 to 10 percent by volume, more preferably 0 to 7 percent by volume, and most preferably 0 to 5 percent by volume with the objective of precluding gasoline coking in the injectors of an engine.

(V(Ar)) of the gasoline composition is in the range of 0 to 35 percent by volume, preferably 0 to 30 percent by volume, more preferably 0 to 25 percent by volume, and most preferably 0 to 20 percent by volume with the objective of, reducing spark plug smoldering and the ozone-formability of exhaust gas as well as the concentration of benzene contained therein, and avoiding the generation of soot.

V(P), V(O) and V(Ar) are the values obtained by the measurement in accordance with JIS K 2536 "Liquid petroleum products-Testing method of components".

The gasoline composition preferably meets the following conditions:

| | |
|---|---|
| (1) V(BZ) | 0–1 vol. % |
| (2) V(Tol) | 0–30 vol. % |
| (3) V(C$_8$A) | 0–20 vol. % |
| (4) V(C$_9$A) | 0–5 vol. % |
| (5) V(C$_{10}$$^+$A) | 0–3 vol. % |
| (6) V(PA) = 0 or | | when V(PA)≠0, V(MA)/V(PA): greater than 1

| | |
|---|---|
| (7) V(C$_4$) | 0–10 vol. % |
| (8) V(C$_5$) | 10–35 vol. % |
| (9) V(C$_6$) | 10–30 vol. % |
| (10) V(C$_7$ + p) | 10–50 vol. % |
| (11) V(C$_9$+) | 0–10 vol. %. |

V(Bz) denotes the amount of benzene, based on the total gasoline composition and is in the range of 0 to 1 percent by volume, preferably 0 to 0.5 percent by volume. A V(Bz) which is 0–1 volume percent of benzene is contributive to an reduction in the benzene concentration in the exhaust gas.

V(Tol) and V(C$_8$A) denote the amount of toluene and the amount of an aromatic hydrocarbon having 8 carbon atoms, respectively, based on the total gasoline composition. V(Tol) is 0 to 30 percent by volume, preferably 0 to 20 percent by volume, while V(C$_8$A) should be 0 to 20 percent by volume, preferably 0 to 15 percent by volume. The aromatic hydrocarbon having 8 carbon atoms may be either ethylbenzene or xylene (including all positional isomers).

V(C$_9$A) denotes the amount of an aromatic hydrocarbon having 9 carbon atoms, based on the total gasoline composition. V(C$_9$A) is 0 to 5 percent by volume, preferably 0 to 3 percent by volume in order to lower the ozone generating ability of exhaust gas. The aromatic hydrocarbon having 9 carbon atoms may be n-propylbenzene, isopropylbenzene (cumene), ethylmethylbenzene (inclusive of all positional isomers) and trimethylbenzene (inclusive of all positional isomers).

V(C$_{10}$+A) denotes the amount of aromatic hydrocarbons having 10 or more carbon atoms, based on the total gasoline composition. V(C$_{10}$+A) is 0 to 3 percent by volume, preferably 0 to 1 percent by volume, and more preferably 0 percent by volume in order to lower the ozone generating ability of exhaust gas. The aromatic hydrocarbon having 10 or more carbon atoms may be diethylbenzene (inclusive of all positional isomers), dimethylethylbenzene (inclusive of all positional isomers), tetramethylbenzene (inclusive of all positional isomers) and n-butylmethylbenzene (inclusive of all positional isomers).

V(MA) and V(PA) denote the amount of an aromatic hydrocarbon having one alkyl substituent (vol. %) and the amount of an aromatic hydrocarbon having more than two alkyl substituents (vol. %), respectively, based on the total gasoline composition. In the present invention, if V(PA) is 0 or V(MA) is not 0, the ratio of V(MA) to V(PA) is held to 1 or greater, preferably 1.5 or greater, and more preferably 2 or greater.

The above V(Bz), V(Tol), V($C_8$A), V($C_9$A), V($C_{10}$+A), V(MA) and V(PA) are the values determined by a chromatography method in accordance with JIS K 2536 "Liquid petroleum products-Testing Method of components".

V($C_4$) denotes the amount of a hydrocarbon having 4 carbon atoms, based on the total gasoline composition. V($C_4$) is 0 to 10 percent by volume, preferably 0 to 5 percent by volume, and more preferably 0 to 3 percent by volume with the objective of further reducing the amount of evaporative emission. The hydrocarbon having 4 carbon atoms may be any of n-butane, 2-methylbutane (isobutane), 1-butene, 2-butene and 2-methylpropene.

V($C_5$) denotes the amount of an aliphatic hydrocarbon having 5 carbon atoms, based on the total gasoline composition. The lower limit of V($C_5$) is 10 percent by volume, and preferably 15 percent by volume. The upper limit of V($C_5$) is 35 percent by volume, and preferably 30 percent by volume. A concentration of more than 10 percent by volume of the aliphatic hydrocarbon having 5 carbon atoms is contributive to the production of a gasoline composition which is capable of providing an excellent drivability at normal temperatures. A concentration of less than 35 percent by volume of the aliphatic hydrocarbon having 5 carbon atoms is contributive to the production of a gasoline composition which is capable of providing an excellent engine performance at high temperature. With the objective of precluding gasoline coking in the injectors of an engine, it is preferred that the unsaturated hydrocarbon content (V($C_5$O) in the aliphatic hydrocarbon having 5 carbon atoms is 0 percent by volume, or that the ratio of the saturated hydrocarbon content to unsaturated hydrocarbon content (V($C_5$p)/(V($C_5$O), is 1 or greater, preferably 1.5 or greater, more preferably 2 or greater, and most preferably 3 or greater. The saturated aliphatic hydrocarbon having 5 carbon atoms may be n-pentane, 2-methylbutane (isopentane) and 2,2-dimethylpropane (neopentane), while the unsaturated aliphatic hydrocarbon having 5 carbon atoms may be 1-pentene, 2-pentene, 2-methyl-1-butene, 2-methyl-2-butene, and 3-methyl-1-butene.

V($C_6$) denotes the amount of an aliphatic hydrocarbon having 6 carbon atoms, based on the total gasoline composition. The lower limit of V($C_6$) is 10 percent by volume, and preferably 15 percent by volume, while the upper limit of V($C_6$) should be 30 percent by volume, and preferably 25 percent by volume. A concentration of 10 percent by volume or greater of the aliphatic hydrocarbon having 6 carbon atoms is contributive to provide an excellent normal temperature engine performance. A concentration of 30 percent by volume or less of the aliphatic hydrocarbon having 6 carbon atoms is contributive to provide an excellent high temperature drivability. With the objective of precluding gasoline coking in the injectors of an engine, it is preferred that the unsaturated hydrocarbon content (V($C_6$o)) in the C6 aliphatic hydrocarbon is 0 percent by volume, or that the ratio of the saturated hydrocarbon content to unsaturated hydrocarbon content (V($C_6$p)/(V($C_6$o)), is 2 or greater, preferably 3 or greater, more preferably 5 or greater, and most preferably 10 or greater. Specific examples of the saturated hydrocarbon having 6 carbon atoms are n-hexane, 2-methylpentane, 3-methylpentane, 2,2-dimethylbutane, and 2,3-dimethylbutane. Specific examples of the unsaturated hydrocarbon having 6 carbon atoms are 1-hexene, 2-hexene, 3-hexene, 2-methyl-1-pentene, 3-methyl-1-pentene, 4-methyl-1-pentene, 2-methyl-2-pentene, 3-methyl-2-pentene, 4-methyl-2-pentene, 2,3-dimethyl-1-butene, 3,3-dimethyl-1-butene, and 2,3-dimethyl-2-butene.

V($C_7$+P) denotes the amount of a saturated aliphatic hydrocarbon having 7 or more carbon atoms, based on the total gasoline composition. The lower limit of V($C_7$+P) is 10 percent by volume, and preferably 20 percent by volume, while the upper limit of V($C_7$+P) is 50 percent by volume, and more preferably 45 percent by volume. V($C_7$+P) of 10 percent by volume or greater is contributive to the production of a gasoline composition providing an excellent normal temperature drivability, while V($C_7$+P) of 50 percent by volume or less is contributive to provide an excellent high temperature drivability. Specific examples of the saturated aliphatic hydrocarbon having 7 or more carbon atoms are n-heptane, 2-methylhexane, 3-methylhexane, 2,2-dimethylpentane, 2,3-dimethylpentane, 2,4-dimethylpentane, 3,3-dimethylpentane, 3-ethylpentane, and 2,2,3-trimethylbutane.

V($C_9$+) denotes the amount of a hydrocarbon having 9 or more carbon atoms, based on the total gasoline composition. V($C_9$+) is in the range of 0 to 10 percent by volume, and preferably 0 to 5 percent by volume, and more preferably 0 percent by volume. A composition having a V($C_9$+) in this preferred range will provide excellent low- and normal-temperature drivability and will reduce the amount of gasoline which dilutes engine oil so as to preclude increased amounts of exhaust hydrocarbon, engine oil deterioration, and sludge formation.

The above V($C_4$), V($C_5$), V($C_5$P), V($C_5$O), V($C_6$), V($C_6$P), V($C_6$O), V($C_7$+P), and V($C_9$+P) are the values as determined by the following gas chromatography method. These values are measured using a methyl-silicone capillary column 25 to 50 m in length, a helium or nitrogen carrier gas and an FID detector under the conditions of, 0.5 to 1.5 ml/min in gas flow rate, 1:50 to 1:250 in partition ratio, 150 to 250° C. in injection temperature, −10 to 10° C. in initial column temperature, 150 to 250° C. in final column temperature and 150 to 250° C. in detector temperature.

The gasoline composition according to the present invention may contain an oxygen-containing compounds in such an amount that the mass percent of oxygen is 0 to 2.7 and, preferably 0 to 2.0. The content of oxygen in excess of 2.7 mass percent would lead to a decrease in fuel consumption efficiency and in NOx emission.

The oxygen-containing compound described herein encompasses alcohols having 2 to 4 carbon atoms and ethers having 4 to 8 carbon atoms. Eligible oxygen-containing compounds for the gasoline composition include ethanol, methyl-tert-butylether (MTBE), ethyl-tert-butyllether, tert-amylethylether (TAME), and tert-amylethylether, among which the preferred are MTBE and TAME, and the most preferred is MTBE. Methanol is not preferred because it is corrosive and would increase the concentration of aldehyde in exhaust gas.

The sulfur content of the gasoline composition is 50 mass ppm or less, preferably 30 mass ppm or less, more preferably 20 mass ppm or less, and most preferably 10 mass ppm or less. The sulfur content if greater than 50 mass ppm would result in poisoning of after-treatment catalysts, increases in the concentration of NOx, carbon monoxide, and hydrocarbons, and a rise in benzene emission. The term "sulfur content" used herein denotes the sulfur content measured in accordance with JIS K 2541 "Crude oil and petroleum products-Determination of sulfur content".

The unwashed existing gum of the gasoline composition is present in an amount of 20 mg/100 ml or less, and the washed gum should be present in an amount of 3 mg/100 ml or less, and preferably 1 mg/100 ml or less, as measured in accordance with JIS K2261 "Petroleum products-Motor gasoline and aviation fuels-Determination of existent gum-Jet evaporation method". Deviations from these amounts would lead to the formation of deposits in the fuel-injection systems and the occurrence of agglutination in the intake valve.

The gross caloric value of the gasoline composition should be 40,000 J/g or more, preferably 45,000 J/g or more as measured by JIS K 2279 "Crude petroleum and petroleum products-Determination and estimation of heat of combustion".

The oxidation stability of the gasoline composition should be 480 minutes or over, preferably 1,440 minutes or over, as measured in accordance with JIS K 2287 "Testing Method for Oxidation Stability of Gasoline (Induction Period Method)". Oxidation stability less than 480 minutes would lead to the formation of gum during storage of the composition.

The gasoline composition gives a value of 1 or 1a in the copper corrosion test to be conducted at a temperature of 50° C. for 3 hours in accordance with JIS K 2513 "Petroleum products-Corrosiveness to copper-Copper strip test". Copper corrosion test values exceeding 1 would indicate that the composition is capable of causing the corrosion of pipes in a fuel system.

The kerosene content of the gasoline composition is within the range of 0 to 4 percent by volume, based on the total gasoline composition. The term "kerosene content" used herein denotes the content of a hydrocarbon having 13 to 14 carbon atoms (vol. %) based on the total gasoline composition, and is quantitatively determined by a gas chromatographic process in which a methyl-silicone capillary column having a column length of 25 to 50 m is fed with a helium or nitrogen gas at a flow rate of 0.5 to 1.5 ml/min. and a divisional ratio of 1:50 to 1:250 and is operated at an injection temperature of 150 to 250° C., at an initial column temperature of –10 to 10° C., a final column temperature of 150 to 250° C., and a detector temperature of 150 to 250° C.

The above-mentioned base gas oil may be prepared with various gas oil components using conventional known methods. Such components may be straight gas oil derivable from atmospheric distillation of crude oil; vacuum gas oil obtained by applying straight heavy oil or residue obtained by atmospheric distillation to vacuum distillation; hydro-refined gas oil obtained by hydro-refining vacuum gas oil derived from vacuum distillation; hydrodesulfurized gas oil obtained by hydrodesulfurizing straight gas oil under conditions which are more sever than those of normal hydro-refining in a single or multi steps; desulfized or undesulfized gas oil; catalytic cracked gas oil obtained by catalytic cracking vacuum heavy gas oil or desulfized fuel; straight kerosene derivable from atmospheric distillation of crude oil; hydro-refined kerosene obtained by hydro-refining straight kerosene; and cracked kerosene obtained by cracking gas oil fraction derived from atmospheric distillation of crude oil. These components may be used singly or in combination.

The gas oil composition containing the additive of the present invention may contain additives other than the additive of the present invention.

Examples of such gas oil additives are lubricity improvers and cetane number improvers.

Eligible lubricity improvers are carboxylic acid-, ester-, alcohol- and phenol-based ones which may be used singly or in combination. Among these, carboxylic acid- or ester-based lubricity improvers are preferred.

Examples of carboxylic acid-based lubricity improvers are linoleic acid, oleic acid, salicylic acid, palmitic acid, myristic acid, hexadecenoic acid and mixtures thereof.

Examples of ester-based lubricity improvers are carboxylates of glycerin. Carboxylic acids constituting carboxylates are linoleic acid, oleic acid, salicylic acid, palmitic acid, myristic acid, and hexadecenoic acid which may be used singly or in combination.

No particular limitation is imposed on the content of the lubricity improvers. However, the lubricity improver may be blended in a gas oil composition in an amount which is preferably 35 mass ppm or greater, and more preferably 50 mass ppm or greater in order to educe the effects of the lubricity improver, more specifically in order that in a diesel engine mounted with distribution type pumps the increase of driving torque of the pumps during running is suppressed and the wear thereof can be reduced. The upper limit of lubricity improver content is preferably 150 mass ppm, more preferably 100 mass ppm because no further improvement can be expected.

Commercially available products referred to as lubricity improvers are usually sold with the effective components diluted in a suitable solvent. In the case where such commercial products are blended with the gas oil composition, the above-described lubricity improver content denotes the content of such effective components.

Eligible cetane number improvers for the present invention are various compounds which are conventionally known as cetane number improvers in the industry, such as nitric esters and organic peroxides. Preferred are nitric esters. Nitric esters encompass 2-chloroethylnitrate, 2-ethoxyethylnitrate, isopropylnitrate, butylnitrate, primary amyl nitrate, secondary amyl nitrate, isoamyl nitrate, primary hexyl nitrate, secondary hexyl nitrate, n-heptyl nitrate, n-octyl nitrate, 2-ethylhexyl nitrate, cyclohexyl nitrate, and ethylene glycol dinitrate. Among these, preferred are alkyl nitrates having 6 to 8 carbon atoms. These compounds may be used singly or in combination.

A cetane number improver may be blended in the gas oil composition in an amount which is 500 mass ppm or greater, preferably 600 mass ppm or greater, more preferably 700 mass ppm or greater, even more preferably 800 mass ppm or greater, and most preferably 900 mass ppm or greater, based on the total mass of the composition because the resulting gas oil composition can reduce the concentrations of NOx, PM, and aldehyde contained in exhaust gas. Although not restricted, the upper limit of a cetane number improver content is 1,400 mass ppm or less, preferably 1,250 mass ppm or less, more preferably 1,100 mass ppm, and most preferably 1,000 mass ppm or less.

Commercially available products referred to as cetane number improvers are sold with the effective components diluted in a suitable solvent. In the case where such commercial products are blended with the gas oil composition, the above-described cetane number improver content means the content of such effective components.

A gas oil composition containing the additive of the present invention may contain detergents.

Such detergents are ashless detergents such as imide-based compounds; alkenyl succinimides such as polybutenyl succinimides which are synthesized from polybutenyl succinic acid anhydrides and ethylenepolyamines; succinates such as polybutenyl succinate which are synthesized from a polyalcohol such as pentaerythritol and polybutenyl succinate anhydride; polymers which are obtained by copolymerizing dialkylaminoethylmethacrylate, polyethylene glycol methacrylate, and vinylpyrroridone with alkylmethacrylate; and reaction products of carboxylic acid and amine, among which the preferred are alkenyl succinimides and reaction products of carboxylic acid and amine.

There may be used an alkenyl succinimide having a number average molecular weight of 1,000 to 3,000 alone or alternatively a mixture of an alkenyl succinimide having a number average molecular weight of 700 to 2,000 and an alkenyl succinimide having a number average molecular weight of 10,000 to 20,000.

One or more kinds of carboxylic acids may be used for the reaction product. Specific examples of such carboxylic acids are fatty acids having 12 to 24 carbon atoms and aromatic carboxylic acids having 7 to 24 carbon atoms. Fatty acids having 12 to 24 carbon atoms may be linolic acid, oleic acid, palmitic acid, and myristic acid. Aromatic carboxylic acids having 7 to 24 carbon atoms may be benzoic acid and salicylic acid. One or more kinds of amines may be used for the reaction product. Typically, oleic amine may be used but various amines are also eligible.

No particular limitation is imposed on the content of these additives in the gas oil composition. However, these additives may be blended in a gas oil composition in an amount which is preferably 30 mass ppm or greater, more preferably 60 mass ppm or greater and even more preferably 80 mass ppm or greater, based on the total mass of the composition in order to attain the effects of these additives used in combination, more specifically to prevent the fuel injection nozzles from being plugged. A content of these additives of lower than 30 mass ppm might not be effective. Since a too much content would lead to a failure in attaining expected results and increase the amount of NOx, PM and aldehyde in the exhaust gas from a diesel engine, these additives is contained in an amount of preferably 300 mass ppm or less, more preferably 180 mass ppm or less.

Like the above-described cetane number improvers, commercially available products referred to as detergents are sold with the effective components diluted in a suitable solvent. In the case where such commercial products are blended with the gas oil composition, the above-described detergents content denotes the content of such effective components.

Furthermore, other known fuel additives may be added alone or in combination to the inventive gas oil composition. Such additives are cold flow improvers such as ethylene-vinyl acetate copolymers and alkenyl succinimide, phenol- or amine-based oxidation inhibitors, metal deactivators such as salicyliden derivatives, antiicing agents such as polyglycol ether, corrosion inhibitors such as fatty amines and alkenyl succinates, antistatic additives such as anionic-, cationic- and amphoteric-surfactants, dyes such as azo dyes, and silicone-based anti-foam additives.

No particular limitation is imposed on the content of these additional additives in the gas oil composition. Each of the additives may be blended in the gas oil composition in an amount which is preferably 0.5 mass percent or less, more preferably 0.2 mass percent or less.

A gas oil composition comprising a base gas oil, the additive of the present invention, and other gas oil additives are not restricted in its properties and components. However, the gas oil composition will preferably exhibit the following distillation properties:

| | |
|---|---|
| Initial distillation boiling point (IBP 0) | 135–200° C. |
| Running point at 10 vol. % ($T_{10}$) | 155–230° C. |
| Running point at 30 vol. % ($T_{30}$) | 175–260° C. |
| Running point at 50 vol. % ($T_{50}$) | 190–300° C. |
| Running point at 70 vol. % ($T_{70}$) | 220–330° C. |
| Running point at 90 vol. % ($T_{90}$) | 290–350° C. |
| Running point at 95 vol. % ($T_{95}$) | 310–360° C. |
| End point | 330–370° C. |

Because an initial distillation boiling point which is too low would cause gasification of a part of light fractions which are aerated too wide, resulting in an increase in the amount of hydrocarbon accompanied with the exhaust gas, an initial boiling point is 135° C. or higher, preferably 140° C. or higher and more preferably 145° C. or higher. Because an initial boiling point which is too high would adversely affect low temperature startability and drivability of an engine, the upper limit of an initial boiling point is preferably 200° C. or lower.

Because a $T_{(10)}$ which is too low would increase the amount of hydrocarbon emission with the same reason as that of a too low initial boiling point, a $T_{(10)}$ is preferably 155° C. or higher, more preferably 165° C. or higher. Because a too high $T_{(10)}$ would adversely affect low temperature startability and drivability of an engine, the upper limit of $T_{(10)}$ is preferably 230° C. or lower.

A too low $T_{(30)}$ would increase the amount of hydrocarbon emission with the same reason as described above, a $T_{(30)}$ is preferably 175° C. or higher, more preferably 180° C. or higher, more preferably 185° C. or higher. Because a too high $T_{(30)}$ would adversely affect low temperature startability and drivability of an engine, the upper limit of $T_{(30)}$ is preferably 260° C. or lower.

A $T_{(50)}$ is preferably 190° C. or higher, more preferably 195° C. or higher, even more preferably 200° C. or higher in terms of fuel consumption efficiency and the power output of an engine. It is recommended that a $T_{(50)}$ is 300° C. or less such that the concentration of particulate matters in exhaust gas can not be increased.

$T_{(70)}$ also gives an influence on fuel consumption efficiency and the power output of an engine. In order to improve fuel consumption efficiency and enhance the power output of an engine, a $T_{(70)}$ is preferably 220° C. or higher, more preferably 225° C. or higher, even more preferably 230° C. or higher. With the objective of improving low temperature drivability and avoiding the increase of the particulate matters concentration in exhaust gas, a $T_{(70)}$ is preferably 330° C. or lower.

A $T_{(90)}$ is generally 290° C. or higher, preferably 300° C. or higher. With the objective of improving low temperature drivability and avoiding the increase of the particulate matters concentration in exhaust gas, a $T_{(90)}$ is preferably 350° C. or lower.

A $T_{(95)}$ is preferably 310° C. or higher. With the objective of improving low temperature drivability and avoiding the increase of the particulate matters concentration in exhaust gas, a $T_{(90)}$ is more preferably 360° C. or lower.

An end point is preferably 330° C. or higher. With the objective of improving low temperature drivability and avoiding the increase of the particulate matters concentration in exhaust gas, an end point is more preferably 370° C. or lower. The distillation properties (initial boiling point, $T^{10}$, $T^{30}$, $T^{50}$, $T^{70}$, $T^{90}$, and end point) used herein are measured in accordance with JIS K 2254 "Petroleum products-Determination of distillation characteristics".

Although not restricted, the sulfur content of the gas oil composition is preferably 0.05 mass percent or less, more preferably 0.035 mass percent or less, even more preferably 0.02 mass percent or less, further more preferably 0.01 mass percent or less, and still further more preferably 0.005 mass percent or less, with the objective of better durability of an after-treatment catalyst device for exhaust gas and suppression of the corrosion of an engine interior. The term "sulfur content" used herein denotes the sulfur content measured in accordance with JIS K 2541 "Crude oil and petroleum products-Determination of sulfur content".

No particular limitation is imposed on the cetane number index and cetane number of the gas oil composition. However, a cetane number index is preferably 45 or greater, more preferably 48 or greater, and most preferably 50 or greater because the concentration of each NOx, particulate matters, and aldehyde may not be increased in exhaust gas.

The term "cetane index" used herein denotes the value calculated in accordance with "8.4 cetane number calculation method using variables equation" prescribed in JIS K 2280 "Petroleum products-Fuels-Determination of octane number, cetane number and calculation of cetane index". The term "cetane number" used herein denotes the cetane number measured in accordance with "7. Determination of cetane number" prescribed in JIS K 2280.

No particular limitation is imposed on the kinematic viscosity of the gas oil composition. With the objective of control of fuel injection timing and lubricity of the distribution type fuel injection pump equipped in an engine, a kinematic viscosity at 30° C. is preferably 1.7 mm$^2$/s or greater, more preferably 1.9 mm$^2$/s or greater, and even more preferably 2.0 mm$^2$/s or greater. In order to prevent the increase of the particulate matters concentration in the exhaust gas and reduce negative effects on low temperature startability of an engine, a kinematic viscosity at 30° C. is preferably 6.0 mm$^2$/s or less, more preferably 5.0 mm$^2$/s or less, and most preferably 4.5 mm$^2$/s or less. The kinematic viscosity used herein is measured in accordance with JIS K 2283 "Gas oil-Determination of cold filter plugging point".

No particular limitation is imposed on the density at 15° C. of the gas oil composition. However, in order to improve fuel consumption efficiency and the acceleration performance, such a density is preferably 800 kg/m$^3$ or greater. The upper limit of a density at 15° C. is preferably 860 kg/m$^3$ or less, and more preferably 850 kg/m$^3$ or less because the particulate matters concentration in exhaust gas can be reduced. The density used herein is measured in accordance with JIS K 2249 "Crude petroleum and petroleum products-Determination of density and petroleum measurement tables based on a reference temperature (15° C.)".

Although not restricted, the gas oil composition preferably contains paraffins, olefins and aromatics in the following amount.

| Paraffins | 60–95 vol. % |
| Olefins | 5 vol. % or less |
| Aromatics | 5–40 vol. % |

The lower limit of saturates in the gas oil composition is preferably 60 vol. % or greater, more preferably 70 vol. % or greater, and even more preferably 75 vol. % or greater in order to reduce the concentration of each NOx and particulate matters in exhaust gas. In order to maintain excellent low temperature startability and drivability, the upper limit of paraffins is 95 vol. % or less, more preferably 90 vol. % or less and, even more preferably 80 vol. % or less.

The olefins content in the gas oil composition is preferably 5 vol. % or less, more preferably 3 vol. % or less, and even more preferably 1 vol. % or less with the objective of stability of the composition.

Since the aromatics content in the inventive gas oil composition gives influences on fuel consumption efficiency and engine power output, it is preferably 5 vol. % or greater, more preferably 10 vol. % or greater, even more preferably 20 vol. % or greater, and further more preferably 25 vol. % or more. Since the aromatics content also has influences on the concentration of each NOx and particulate matters in the exhaust gas, it is preferably 40 vol. % or less, more preferably 35 vol. % or less, and most preferably 30 vol. % or less.

The terms "paraffins olefins" and "aromatics" used herein denotes the values obtained by measurement in accordance with JIS K 2536 "Liquid petroleum products—Testing Method of Components".

No particular limitation is imposed on the pour point (PP) of the gas oil composition. However, with the objective of low temperature startability and drivability, PP is preferably 0° C. or lower, more preferably −5° C. or lower, and most preferably −10° C. or lower. With the objective of lubricity in the fuel injection pump, PP is preferably −20° C. or higher, more preferably −15° C. or higher, even more preferably −10° C. or higher, further even more preferably −5° C. or higher, and most preferably 0° C. or higher. The term "pour point (PP)" used herein denotes the pour point measured in accordance with JIS K 2269 "Testing Methods for Pour Point and Cloud point of Crude Oil and Petroleum Products".

No particular limitation is imposed on the cold filter plugging point (CFPP) of the gas oil composition. However, a CFPP is preferably 0° C. or lower, more preferably −5° C. or lower, even more preferably −10° C. or lower, and most preferably −20° C. or lower. With the objective of better lubricity in the fuel injection pump, a CFPP is preferably −15° C. or higher, more preferably −10° C. or higher, even more preferably −5° C. or higher, and most preferably 0° C. or higher.

The term "CFPP" used herein denotes the plugging point measured in accordance with JIS K 2288 "Gas oil—Determination of cold filter plugging point".

No particular limitation is imposed on the cloud point(CP) of the gas oil composition. However, the cloud point (CP) is preferably 0° C. or lower. The term "cloud point (PP)" used herein denotes the cloud point measured in accordance with JIS K 2269 "Testing Methods for Pour Point and Cloud point of Crude Oil and Petroleum Products".

Examples of the invention will now be provided, with the understanding that the invention is no way limited by these examples.

Before describing the examples, synthesis examples of compounds having a group represented by formula (1) will be presented.

SYNTHESIS EXAMPLE 1

(Compound 1)

[Compound 1]

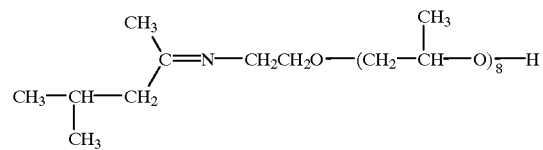

61.1 g (1.0 mole) of ethanolamine and 130.2 g (1.3 mole) of methyl isobutyl ketone were charged into a 500 ml 4-neck flask equipped with a reflux condenser and a thermometer and refluxed at 115° C. for 20 hours, followed by removal of 17.5 mL water resulting from the reaction. Thereafter, 131.8 g of a ketimine compound were obtained by distilling out the excess methyl isobutyl ketone, the unreacted ethanolamine, and the water remaining in the system.

71.6 g (0.5 mole) of the ketimine compound and 5.6 g (0.1 mole) of potassium hydroxide were charged into a 1 L autoclave. After the autoclave atmosphere was filled with nitrogen gas, the autoclave was heated to 90° C. so as to distil out the resulting water. Thereafter, 100 ml of toluene and 232.0 g (4.0 moles) of propyleneoxide were charged into the autoclave and reacted at 95° C. for 5 hours. After the reaction, the reaction product was neutralized with a solid acid and filtered, followed by distilling out the solvent, i.e., toluene, thereby obtaining 285.0 g of an oily liquid product (Compound 1).

removal of 17.2 mL water resulting from the reaction. Thereafter, 146.7 g of a ketimine compound were obtained by distilling out the excess methyl ethyl ketone, the unreacted 4-aminophenole, and the water remaining in the system.

81.5 g (0.5 mole) of the ketimine compound and 5.6 g (0.1 mole) of potassium hydroxide were charged into a 1 L autoclave. After the autoclave atmosphere was filled with nitrogen gas, the autoclave was heated to 90° C. so as to distil out the resulting water. Thereafter, 100 ml of toluene and 435.0 g (7.5 moles) of propyleneoxide were charged into the autoclave and reacted at 95° C. for 5 hours. After the reaction, the reaction product was neutralized with a solid acid and filtered, followed by distilling out the solvent, i.e., toluene, thereby obtaining 465.5 g of an oily liquid product (Compound 3).

SYNTHESIS EXAMPLE 4

(Compound 4)

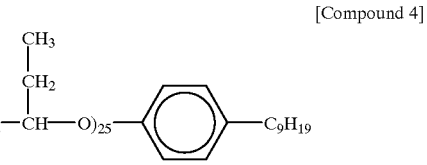

[Compound 4]

SYNTHESIS EXAMPLE 2

(Compound 2)

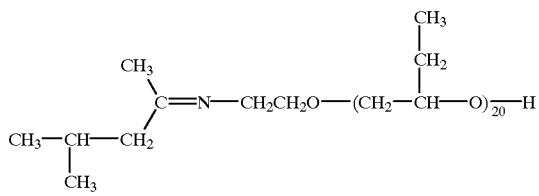

[Compound 2]

745.5 g of an oily liquid product was obtained by following the procedures of Example 1 except that 720.0 g (10.0 moles) butyleneoxide was used instead of 232.0 g propyleneoxide.

SYNTHESIS EXAMPLE 3

(Compound 3)

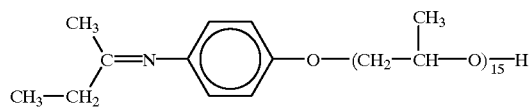

[Compound 3]

109.0 g (1.0 mole) of 4-aminophenole and 108.0 g (1.5 mole) of methyl ethyl ketone were charged into a 500 ml 4-neck flask equipped with a reflux condenser and a thermometer and refluxed at 115° C. for 20 hours, followed by 110.0 g (0.5 mole) of nonylphenol and 5.6 g (0.1 mole) of potassium hydroxide were charged into a 2 L autoclave. After the autoclave atmosphere was filled with nitrogen gas, the autoclave was heated to 90° C. Thereafter, 200 mL of toluene and 900.0 g (12.5 moles) of 1,2-butyleneoxide were charged into the autoclave and reacted at 120° C. for 5 hours. After completion of the reaction, the reaction product solution was neutralized with hydrochloric acid, followed by distilling out the solvent, i.e., toluene thereby obtaining 927.5 g of a polyoxyalkylene compound.

40.0 g (0.41 mole) of liquid phosgene were added to a mixed solution of 404.0 g of the polyoxyalkylene compound corresponding to 0.2 mole which was calculated from the weight-average molecular weight and 100 mL of toluene, at of 0° C. and then reacted at room temperature for 12 hours while cooling the reflux tube with dry ice. After completion of the reaction, 377.5 g of a chlorine-containing compound was obtained by removing the excess phosgene and distilling out the solvent, i.e., toluene.

After a mixed solution of 100 mL of toluene, 100 mL of pyridine, and 120.0 g (2.0 moles) of ethylenediamine was cooled to 5° C., 364.5 g, corresponding to 0.18 mole calculated from the average-weight molecular weight, of the chlorine-containing compound was added dropwise thereto and reacted for 3 hours with maintaining the system at 5° C. The reaction was continued at room temperature for 2 hours. After completion of the reaction, the reaction product was purified by removing the unreacted ethylenediamine, the hydrochloric acid salt thus formed, and the solvent, i.e., toluene, thereby obtaining 342.5 g of polyetheramine.

325 g of the polyetheramine corresponding to 0.15 mole calculated from the average-weight molecular weight and 100 g (1.0 mole) of methyl isobutyl ketone were charged into a 1 L 4-neck flask and refluxed at 115° C. for 20 hours, followed by removal of 2.7 mL of water resulting from this reaction. Thereafter, the reaction product was purified by distilling out the excess methyl isobutyl ketone and the water remaining in the system, thereby obtaining 300.0 g of an oily liquid product (Compound 4).

SYNTHESIS EXAMPLE 5

(Compound 5)

[Compound 5]

$$CH_3 \diagdown C=N-CH_2-CH-CH_2-(C-CH_2)_{16}-C-CH_3$$
with $CH_3-CH-CH_2$ on the left branch with $CH_3$, and $CH_3$ groups on the middle and right carbons.

205.0 g (0.2 mole) of a commercially available polybutenylamine and 100.0 g (1.0 mole) of methyl isobutyl ketone were charged into a 500 mL 4-neck flask equipped with a reflux condenser and a thermometer and refluxed at 115° C. for 20 hours, followed by removal of 3.5 mL water resulting from the reaction. Thereafter, the reaction product was purified by distilling out the excess methyl isobutyl ketone and the water remaining in the system thereby obtaining 210.0 g of an oily liquid product (Compound 5).

SYNTHESIS EXAMPLE 6

(Compound 6)

[Compound 6]

$$CH_3 \diagdown C=N-\text{cyclohexyl}$$
$$CH_3-CH-CH_2 \diagup$$
$$CH_3$$

98.0 g (1.0 mole) of cyclohexylamine and 130.2 g (1.3 mole) of methyl isobutyl ketone were charged into a 500 mL 4-neck flask equipped with a reflux condenser and a thermometer and refluxed at 115° C. for 20 hours, followed by removal of 17.0 mL water resulting from the reaction. Thereafter, the reaction product was purified by distilling out the excess methyl isobutyl ketone, the unreacted cyclohexylamine, and the water remaining in the system thereby obtaining 162.0 g of an oily liquid product (Compound 6).

SYNTHESIS EXAMPLE 7

(Compound 7)

[Compound 7]

$$CH_3 \diagdown \qquad\qquad CH_3 \diagup$$
$$C=N-CH_2CH_2-N-CH_2CH_2-N=C$$
$$CH_3-CH-CH_2 \qquad H \qquad CH_2-CH-CH_3$$
$$CH_3 \qquad\qquad\qquad\qquad\qquad CH_3$$

103.0 g (1.0 mole) of diethylenetriamine and 260.4 g (2.6 moles) of methyl isobutyl ketone were charged into a 500 mL 4-neck flask equipped with a reflux condenser and a thermometer and refluxed at 115° C. for 20 hours, followed by removal of 35.0 mL water resulting from the reaction. Thereafter, the reaction product was purified by distilling out the excess methyl isobutyl ketone, the unreacted diethylenetriamine, and the water remaining in the system thereby obtaining 240.0 g of an oily liquid product (Compound 7).

INVENTIVE EXAMPLES 1–7, AND COMPARATIVE EXAMPLES 1–3

A base gasoline (internal combustion engine gasoline) having the following properties was prepared by mixing 60 parts by volume of catalytic reformed gasoline, 30 parts by volume of catalytic cracked gasoline, and 10 parts by volume of alkylate.

| Base gasoline properties | |
|---|---|
| Reid vapor pressure | 0.64 kgf/cm$^2$) |
| Specific gravity | 0.729 |
| Boiling range | 30–190° C. |
| Octane number | 98.1 |

Each of fuel compositions of Inventive Examples 1–7 shown in Table 1 below was prepared by adding 0.04 percent by mass of an additive which is a compound having a group of formula (1) of the present invention to the above base gasoline.

The following engine evaluating tests were conducted for each of the fuel compositions. For the comparison purpose, the same tests were conducted for the cases in which a base gasoline was used alone (Comparative Example 1) and in which a polybutenylamine-based detergent was used instead of the compound having a group of formula (1) of the present invention (Comparative Examples 2 and 3). The results were shown in Table 1.

[Engine Evaluating Test]

(1) Detergency test in intake systems

A passenger car equipped with a 2000 ml displacement fuel injector engine was used, and after repeating the following running mode, of which one cycle is 1 hour, for 200 hours and the engine was disassembled to measure the amount of deposits on the intake valves. The detergency was evaluated on the basis of differences in the amount of deposits between the run with the base gasoline alone (Comparative Example 1) and the runs with the fuel compositions obtained above.

The engine used for this test was disassembled prior to the test so as to remove deposits from the combustion chamber and the intake system and was equipped with new intake valves, exhaust valves and spark plugs all of which had been weighed and was filled with a new engine oil.

Running Mode

Idling: 1 minute

Engine operating at 1,500 rpm with an intake negative pressure of $-2.66 \times 10^4$Pa ($-200$ mmHg):30 minutes Engine operating at 2,700 rpm with an intake negative pressure of $-4 \times 10^4$Pa ($-300$ mmHg):20 minutes Engine stopped: 9 minutes (2) Detergency test in combustion chamber A passenger car equipped with a 2000 ml displacement fuel injection engine was used and the above fuel compositions were used as a fuel. The car was driven at 1,500 rpm with an intake pressure of $-2 \times 10^4$Pa ($-150$ mmHg) and at a coolant temperature of 50° C. for 96 hours. The engine was disassembled to measure the amount of the deposits in the combustion chamber. The detergency was evaluated with the difference between this amount and the deposits amount obtained by using the base gasoline only (Comparative Example 1). The engine used for this test was disassembled prior to the test to remove deposits from the combustion chamber and the intake system and was equipped with new intake valves, exhaust valves and spark plugs all of which had been weighed and be filled with a new engine oil.

TABLE 1

| | | Engine evaluation test results | |
|---|---|---|---|
| | Additive | Varied deposits (mg) in intake system 3) | Varied deposits (mg) in combustion chamber 4) |
| Inventive Example 1 | Compound 1 | −105.2 | −182.8 |
| Inventive Example 2 | Compound 2 | −85.6 | −132 |
| Inventive Example 3 | Compound 3 | −89.1 | −103.2 |
| Inventive Example 4 | Compound 4 | −89.7 | −75.6 |
| Inventive Example 5 | Compound 5 | −90.3 | −95.3 |
| Inventive Example 6 | Compound 6 | −62.4 | −59.2 |
| Inventive Example 7 | Compound 7 | −49.6 | −48.8 |
| Comparative Example 1 | — | | |
| Comparative Example 2 | polybutenyl-amine-based 1) | −52.5 | +419.7 |
| Comparative Example 3 | polybutenyl-amine-based 2) | −61.3 | +772.1 |

1) Polybutenylamine detergent 1 active component: imide (number average molecular weight about 3,000) of polybutenyl succinate and tetraethylene pentamine
2) Polybutenylamine detergent 2 active component: polybutenyl tetraethylene pentaime (number average molecular weight about 3,500)
3) Varied deposits in intake system: difference compared with base gasoline alone
4) Varied deposits in combustion chamber: difference compared with base gasoline alone As clearly shown by the engine evaluation test results in Table 1, the fuel compositions of Examples 1–7 exhibited significantly enhanced deposit detergency effect upon intake systems and combustion chambers. Whereas, the fuel composition of Comparative Example 1 which does not contain an additive was poor in deposit detergency in the intake system, while those of Comparative Examples 2 and 3 both of which contain commercially available polybutenylamine detergents were contributive to deposit detergency at the intake system but conversely to increase deposits in the combustion chamber, compared to the base gasoline alone.

INVENTIVE EXAMPLES 8–14 AND COMPARATIVE EXAMPLE 4

Gas oil compositions of Inventive Examples 8–14 were prepared by adding 0.01 percent by mass of each of the compound used in Inventive Examples 1–7 to a base gas oil with the properties below.

The engine nozzle detergency test described below was conducted for each of the gas oil compositions. The results were shown in Table 2. For the comparison purpose, the same test was conducted for the base gas oil alone (Comparative Example 4). The results are also shown in Table 2.

[Detergency test in nozzles]

A 2 L total displacement engine with 4 valves was operated at 1,840 rpm with a torque of 36,4 Nm for 48 hours and after the test the residual gas oil flow ratio in the nozzles was measured. The term "residual flow ratio" denotes a ratio of the flow in the nozzle after the test to that in a new nozzle before the test.

The nozzle flow rate was measured when the needle valve is lifted to 0.1 mm. Greater residual flow rate indicates more excellent detergency.

| Base gas oil properties | |
|---|---|
| Cetane number | 54 |
| Cetane index | 54 |
| Distillation Property | ° C. |
| Initial boiling point | 164 |
| $T_{10}$ | 205 |
| $T_{30}$ | 254 |
| $T_{50}$ | 282 |
| $T_{70}$ | 305 |
| $T_{90}$ | 335 |
| $T_{95}$ | 348 |
| Distillation end point | 361 |
| Sulfur content mass ppm | 380 |
| Kinematic viscosity @30° C. mm$^2$/s | 3.659 |
| Density @15° C. kg/m$^3$ | 834.0 |
| Composition analysis volume % | |
| Saturates | 73.6 |
| Olefins | 0.1 |
| Aromatics | 26.3 |
| Pour point ° C. | −17 |
| Plugging point ° C. | −9 |

TABLE 2

| | Inventive Example | | | | | | | Comparative |
|---|---|---|---|---|---|---|---|---|
| | 8 | 9 | 10 | 11 | 12 | 13 | 14 | Example 4 |
| Additive | Compound 1 | Compound 2 | Compound 3 | Compound 4 | Compound 5 | Compound 6 | Compound 7 | — |
| Nozzle residue flow ratio (%) | 57 | 54 | 53 | 48 | 55 | 47 | 42 | 35 |

As clearly shown by the nozzle detergency test results shown in Table 2, the gas oil compositions of Examples 8–14 exhibited significantly excellent detergency of deposits in the injection nozzles. Whereas, the gas oil composition of Comparative Example 4 which did not contain the additive was poor in detergency of deposits build-up in the injection nozzles, resulting in reduced fuel flow.

The use of the additive comprised of a compound having a group represented by formula (1) in accordance with the invention makes it possible to produce a fuel composition which exhibits superior detergency effect even under a severe condition such as where the engine was operated under a cold condition.

What is claimed is:

1. A detergent for gasoline or gas oil comprising a compound having a group represented by the formula (2)

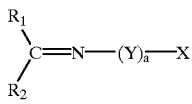
(2)

wherein $R^1$ and $R^2$ are each independently a hydrocarbon group having 1 to 30 carbon atoms, X is selected from the group consisting of X1 and X3 groups, Y is selected from the group consisting of Y1, Y2, Y3 and Y4 groups, and a is an integer of 0 or 1;

X1 being a group represented by the formula (3)

(3)

wherein A is an alkylene group having 2 to 18 carbon atoms, b is an integer from 2 to 200, and $R^3$ is selected from the group consisting of hydrogen and a hydrocarbon group having 1 to 300 carbon atoms;

X3 is a group having a nitrogen-containing cyclic compound residue, represented by the formula (5)

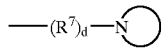
(5)

wherein $R^7$ is an alkylene group having 2 to 6 carbon atoms, the cyclic compound may contain, in addition to the nitrogen bonded to $R^7$, oxygen, hydrogen, carbon, and nitrogen, and d is an integer of 0 or 1; and Y1 being a group represented by the formula (6)

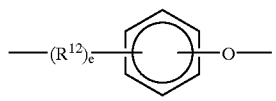
(6)

wherein $R^{12}$ is an alkylene group having 2 to 6 carbon atoms, and e is an integer of 0 or 1, Y2 being a group represented by the formula (7)

(7)

wherein $R^{13}$ is an alkylene group having 2 to 6 carbon atoms, and f is an integer of 0 or 1, Y3 being a group represented by the formula (8)

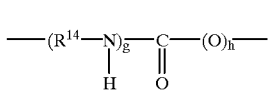
(8)

wherein $R^{14}$ is an alkylene group having 2 to 6 carbon atoms, g is an integer from 1 to 5, and h is an integer of 0 or 1, and Y4 being a group represented by the formula (9)

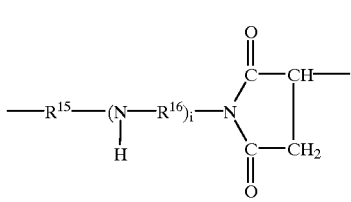
(9)

wherein $R^{15}$ and $R^{16}$ are each independently an alkylene group having 2 to 6 carbon atoms, and i is an integer from 0 to 5.

2. The detergent according to claim 1 wherein said compound is represented by formula (2) wherein $R^1$ and $R^2$ are each selected from the group consisting of a straight alkyl group having 1 to 12 carbon atoms, a branched alkyl group having 3 to 12 carbon atoms, an aryl group having 6 to 18 carbon atoms, and an alkylaryl group having 7 to 18 carbon atoms, X is selected from the group consisting of X1 and X3 groups, Y is selected from the group consisting of Y1, Y2, Y3 and Y4 groups, and a is an integer of 0 or 1;

X1 being a group represented by formula (3) wherein $R^3$ is selected from the group consisting of hydrogen, a straight alkyl group having 1 to 12 carbon atoms, a branched alkyl group having 3 to 12 carbon atoms, a cycloalkyl group, an aryl group having 6 to 18 carbon atoms, an alkylaryl group having 7 to 18 carbon atoms, a residue derived from polypropylene having a weight-average molecular weight of 500 to 3,000, and a residue derived from polyisobutylene having a weight average molecular weight of 500 to 3,000, A is an alkylene group having 2 to 6 carbon atoms, and b is an integer from 2 to 200, X3 being a group having a nitrogen-containing cyclic compound residue, represented by formula (5) wherein $R^7$ an alkylene group having 2 to 4 carbon atoms, the nitrogen-containing compound residue is the residue of a compound selected from the group consisting of piperidine, piperazine, morpholine, and either one of them to which an alkyl group having 1 to 6 carbon atoms bonds, and d is an integer of 0 or 1; and Y1 being a group of formula (6) wherein $R^2$ is an alkylene group having 2 to 4 carbon atoms, and e is an integer of 0 or 1; and Y2 being a group of formula (7) wherein $R^{13}$ is an alkylene group having 2 to 4 carbon atoms, and f is an integer of 0 or 1, Y3 being a group of formula (8) wherein $R^{14}$ an alkylene group having 2 to 4 carbon atoms, g is an integer from 1 to 4, and h is an integer of 0 or 1, and Y4 being a group of formula (9) wherein $R^{15}$ and $R^{16}$ are each independently an alkylene group having 2 to 4 carbon atoms, and i is an integer form 0 to 4.

3. The detergent according to claim 1 wherein said compound is represented by formula (2) wherein $R^1$ and $R^2$ are each independently selected from the group consisting of a straight alkyl group having 1 to 6 carbon atoms, a branched alkyl group having 3 to 6 carbon atoms, a phenyl group, a straight alkylaryl group having 7 to 15 carbon atoms and a branched alkylaryl group having 9 to 15 carbon atoms, X is an X1 group, Y is selected from the group consisting of Y1, Y2, Y3, and Y4 groups, and a is an integer of 0 or 1;

X1 being a group of formula (3) wherein $R^3$ is selected from the group consisting of hydrogen, a straight alkyl group having 1 to 6 carbon atoms, a branched alkyl group having 3 to 6 carbon atoms, a cycloalkyl group, a phenyl group, an alkylaryl group having 7 to 15 carbon atoms, and a residue derived from polyisobutylene having a weight-average molecular weight of 700 to 2,000, A is an alkylene group having 2 to 4 carbon atoms, and b is an integer from 2 to 100; and Y1 being a group of formula (6) wherein e is 0, Y2 being a group of formula (7) wherein f is 0, Y3 being a group of formula (8) wherein $R^{14}$ selected from the group consisting of ethylene, propylene and trimethylene groups, g is an integer from 1 to 3, and h is 1, and Y4 being a group of formula (9) wherein $R^{15}$ and $R^{16}$ are each independently selected from the group consisting of ethylene, propylene, and trimethylene groups, and i is an integer from 0 to 3.

4. The detergent according to claim 1 wherein $R^1$ and $R^2$ are each independently selected from the group consisting of a straight alkyl group having 1 to 4 carbon atoms, a branched alkyl group having 3 to 4 carbon atoms, a phenyl group, a straight alkylaryl group having 7 to 15 carbon atoms and a branched alkylaryl group having 9 to 15 carbon atoms, X is a group of X1, Y is selected from the group consisting of Y1 and Y3 groups, and a is an integer of 0 or 1;

X1 is a group of formula (3) wherein $R^3$ is selected from the group consisting of hydrogen, a straight alkyl group having 1 to 6 carbon atoms, a branched alkyl group having 3 to 6 carbon atoms, a cyclohexyl group, a phenyl group, an alkylaryl group having 7 to 15 carbon atoms, and a residue derived from polyisobutylene having a weight-average molecular weight of 700 to 1,500, A is an alkylene group having 2 to 4 carbon atoms, and b is an integer from 2 to 100; and Y1 being a group of formula (6) wherein e is 0, and Y3 being a group of formula (8) wherein $R^{14}$ is selected from the group consisting of ethylene, propylene groups, g is an integer of 1 or 2, and h is 1.

5. A fuel composition comprising a gasoline or a gas oil and the detergent as defined in claim 1.

* * * * *